US008979754B2

(12) United States Patent
Sulkin et al.

(10) Patent No.: US 8,979,754 B2
(45) Date of Patent: Mar. 17, 2015

(54) INTERACTIVE SYSTEM AND METHOD FOR NEUROMOTOR FUNCTIONING ASSESSMENT AND TRAINING

(75) Inventors: Adi Sulkin, Ramat Aviv (IL); Esther Sulkin, Ramat Aviv (IL)

(73) Assignee: FITS—Functional Interactive Timing System Ltd., Tel Aviv (IL)

( * ) Notice: Subject to any disclaimer, the term of this patent is extended or adjusted under 35 U.S.C. 154(b) by 1043 days.

(21) Appl. No.: 11/836,184

(22) Filed: Aug. 9, 2007

(65) Prior Publication Data

US 2009/0043170 A1 Feb. 12, 2009

(51) Int. Cl.
*A61B 5/00* (2006.01)
*A61B 5/16* (2006.01)
*A61B 5/103* (2006.01)
*A61B 5/11* (2006.01)
*G09B 23/28* (2006.01)

(52) U.S. Cl.
CPC ............... *A61B 5/162* (2013.01); *A61B 5/1038* (2013.01); *A61B 5/1124* (2013.01); *A61B 5/1126* (2013.01); *A61B 5/6825* (2013.01); *A61B 5/6829* (2013.01); *G09B 23/28* (2013.01)
USPC .......................................................... 600/300

(58) Field of Classification Search
None
See application file for complete search history.

(56) References Cited

U.S. PATENT DOCUMENTS

| | | | | |
|---|---|---|---|---|
| 4,894,777 A * | 1/1990 | Negishi et al. | ................ | 600/558 |
| 5,629,985 A | 5/1997 | Thompson | | |
| 5,876,334 A * | 3/1999 | Levy | ............................. | 600/300 |
| 6,193,153 B1 | 2/2001 | Lambert | | |
| 6,475,161 B2 * | 11/2002 | Teicher et al. | ................ | 600/558 |
| 6,546,134 B1 * | 4/2003 | Shrairman et al. | ............ | 382/186 |
| 6,719,690 B1 | 4/2004 | Cassily | | |
| 6,865,519 B2 * | 3/2005 | Lampert et al. | ............... | 702/189 |
| 7,122,004 B1 * | 10/2006 | Cassily | ......................... | 600/300 |
| 7,528,315 B2 * | 5/2009 | Goodwin | ........................ | 84/611 |
| 7,762,264 B1 * | 7/2010 | Ramig et al. | .................. | 128/898 |
| 2002/0055383 A1 * | 5/2002 | Onda et al. | ....................... | 463/36 |
| 2002/0111540 A1 * | 8/2002 | Schmidt et al. | ............... | 600/300 |
| 2004/0158297 A1 * | 8/2004 | Gonzalez | ......................... | 607/45 |
| 2006/0100021 A1 * | 5/2006 | Yoshino et al. | ................ | 463/45 |
| 2007/0155588 A1 | 7/2007 | Stark | | |
| 2007/0299319 A1 * | 12/2007 | Chan et al. | ..................... | 600/300 |

OTHER PUBLICATIONS

International Search Report mailed on Nov. 19, 2008 for PCT/IL2008/01045.
Written Opinion of the International Searching Authority mailed on Nov. 19, 2008 for PCT/IL2008/01045.
Rebecca M. C. Spencer, Richard B. Ivry, Howard N. Zelaznik, "Roll of the cerebellum in movements: Control of timing or movements translations?", 2004.

* cited by examiner

*Primary Examiner* — William Thomson
*Assistant Examiner* — Bobby Soriano
(74) *Attorney, Agent, or Firm* — Oliff PLC

(57) ABSTRACT

The present invention discloses an interactive system for neuromotor functioning assessment and training of a subject, using rhythmic-based techniques. The system may include an acquisition unit and an analysis unit connected by communication means. The acquisition unit may include measuring devices and may enable producing rhythmic aural and/or visual indications and measuring the subject's performing of actions under the produced rhythms. The actions may be carried out according to predefined exercises using the measuring devices. The analysis unit may include a software application that allows receiving, storing, displaying and analyzing of acquisition data arriving from the acquisition unit. At least one of the measuring devices may be a graphic-tool such as, for example, a digital pen connected to a receiver, enabling to measure the subject's lifting of the hand while performing graphical actions such as writing.

31 Claims, 9 Drawing Sheets

INTERACTIVE SYSTEM AND METHOD FOR NEUROMOTOR FUNCTIONING ASSESSMENT AND TRAINING

FIELD OF TUE INVENTION

Figure 1:
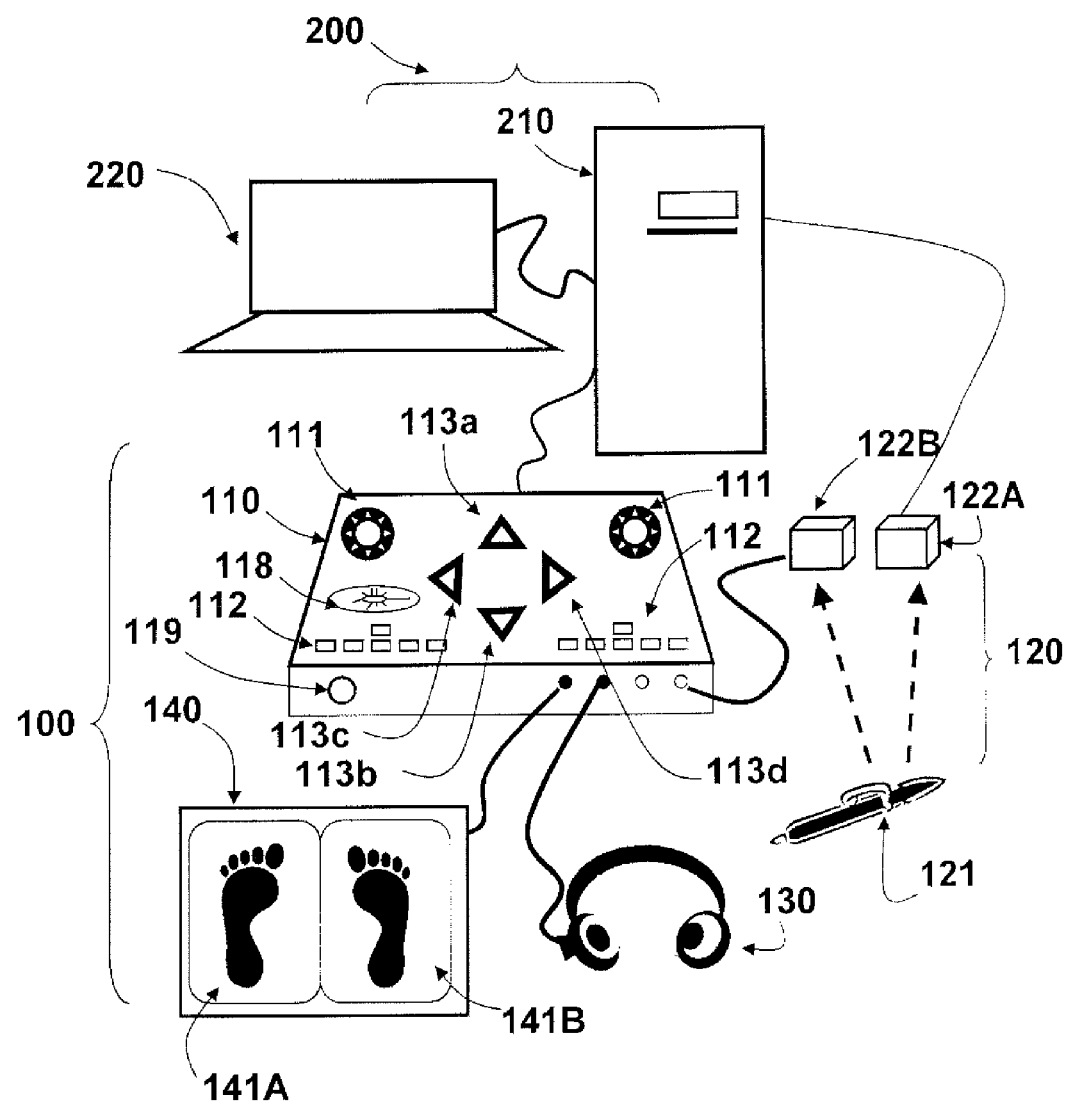

The present invention generally relates to the field of behavioral functioning diagnosing techniques. More particularly, the present invention relates to interactive rhythmus-based systems for assessing neuromotor functioning and learning skills.

BACKGROUND OF THE INVENTION

Today, there is a growing awareness of parents, teachers and therapists regarding the connections between neuromotor functioning of subjects and the subjects' learning skills and other behavioral, psychological and mental problems, disorders and the like.

A subject may be any human tested or, trained for identifying learning skills related problems such as toddlers, children and the like.

Many learning-related disorders such as dyslexia, dysgraphia, Attention Deficit Hyperactivity Disorder (ADHD) and many more are found to be neurological disorders that may affect the subject's learning abilities such as concentration, speed of thought, reading and writing and the like. Therefore, diagnosing problems in certain motor activities may relate to or indicate the subject's learning skills or behavioral difficulties.

Studies show a clear connection between the brain's ability to automate physical activities and the level of timing functioning (mainly controlled by the cerebellum an area in the brain that is responsible for the regulation and coordination of complex voluntary muscular movements as well as the maintenance of posture and balance) and the subject's learning skills, learning and behavioral disorders. For example, subjects with cerebellum damage may show difficulties in performing timed tasks {see Rebecca M. C. Spencer, Richard B. Ivry, Howard N. Zelaznik, "Roll of the cerebellum in movements: Control of timing or movements translations?", 2004}.

Studies have shown that exercises involving requiring subjects to maintain monotonic and/or rhythmic physical activity while performing different actions such as reading, writing, speaking and the like may be a powerful tool both for diagnosing the subject's level of neuromotor functioning, as well as for training subjects with low neuromotor functioning to improve the subjects' learning skills and behavior.

Recent studies reveal that the neuromotor functioning of a subject may be estimated and graded when a subject performs refined exercises in which he/she performs fine graphical actions such as writing the alphabet letters or copying shapes while following a metronome monotonic rhythmus—writing a letter per a metronome-nock, for example.

A patent number U.S. Pat. No. 6,719,690 by Cassily James F. discloses a timing, assessment tool that is manipulatable by a user in response to the user's expected occurrence of a rhythmic reference signal. The timing assessment tool derives a rhythmic assessment from a pattern of user responses to the user's expected occurrence of the rhythmic reference signal. An analyzer, which may include a database, is provided to respond to the rhythmic assessment to indicate a diagnosis and/or corrective intervention. Cassily's tool include sensing devices such as hand and feet sensors measuring the responses of a user to the rhythmic signal.

Cassily's patent enables measuring the time-shifts between the subject's responses under a heard or visually displayed rhythmus and the actual rhythm played by the system. Those shifts indicate the neurological pattern and functioning of the subject.

SUMMARY OF THE INVENTION

The present invention is an interactive system and a method for measuring, analyzing and presenting of neuromotor functioning-assessments of at least one subject to facilitate in assessing the subject's learning and behavioral skills by measuring the subject's neuromotor performances, using various measuring devices used according to various exercising techniques. The system may comprise an acquisition unit and an analysis unit, where the two units may be connected by any communication means known in the art to allow the acquisition unit to transmit acquisition data to the analysis unit where the data can be analyzed.

According to some embodiments of the present invention, the acquisition unit may include measuring devices that may allow measuring the subject's performances of predefined exercises that include rhythmic operation of actions that involve using those devices.

Additionally, at least part of the actions of each exercise may be performed by the subject according to a predefined rhythmus applied to the subjects through aural and/or visual indications. For example, the system may produce a metronomic sound transmitted to the subject by aural means such as speakers and/or earphones, where the system may require the subject to perform the actions according to the rhythm that is produced.

The exercises and data acquisition may be supervised by a user that may be any person responsible for testing the subject. For example, the user may be a teacher, a parent, a psychologist and the like.

Additionally, the analysis unit may comprise a software application that may enable inputting, receiving, storing, displaying and analyzing of acquisition data arriving from the acquisition unit as well as remote tuning of at least some of the devices.

According to some embodiments of the present invention, the measuring devices may include a graphic-tool that may be, for example, a digital pen connected to a pen receiver or a digital touch screen enabling to sense movements of a pen like instrument. The pen, for example, may allow sensing the subject's hand movements when performing graphic actions of a graphic exercise and assessing the subjects graphic and didactic neuromotor functioning, according to the subject's performing of said actions.

For example, the exercises may involve writing the alphabet letters according to a metronomic constant rhythmus, where the system may measure the timing parameters of the subject's hand lifts comparing these parameters with the timing parameters of the rhythmus, where the distance between the measured and the produced timing may be defined as a time shift. The time shifts may indicate the subject's neuromotor functioning, where the shifts (as part of the acquisition data) may be compared to reference shifts defined in the analysis unit as part of a reference data.

The acquisition unit may additionally include a stepper. The stepper may include a plurality of pads that may allow sensing the subject's stepping impact upon each pad.

According to some embodiments of the invention, the acquisition unit may comprise an acquisition box connected to the measuring device, at least some of the aural transmitting devices such as the earphones and to the analysis unit, enabling to transmit the acquisition data to the analysis unit by any communication means known in the art.

According to some embodiments of the present invention, the acquisition box may comprise at least one sound producer; at least one speaker; visual indicators; at least one keypad; and input and output portals. The box may enable producing aural rhythmic indication using the speakers, the earphones and visual rhythmic indication using the visual indicators and acquiring measuring data from the connected and/or integrated measuring devices such as the keypad, the stepper and the graphic-tool.

BRIEF DESCRIPTIONS OF THE DRAWINGS

The subject matter regarded as the invention will become more clearly understood in light of the ensuing description of embodiments herein, given by way of example and for purposes of illustrative discussion of the present invention only, with reference to the accompanying drawings, wherein FIG. 1 is a schematic illustration of a system for assessing neuromotor and behavioral functioning assessing and training, according to some embodiments of the present invention.

Figure 2:
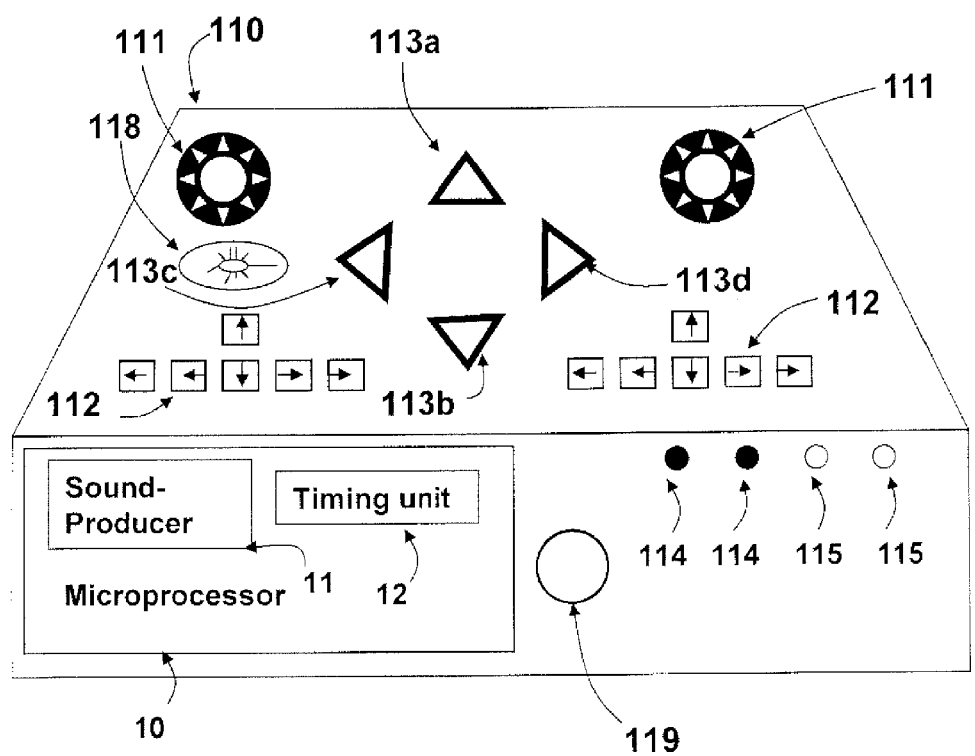

FIG. 2 schematically illustrates an acquisition box, according to some embodiments of the present invention.

Figure 3:
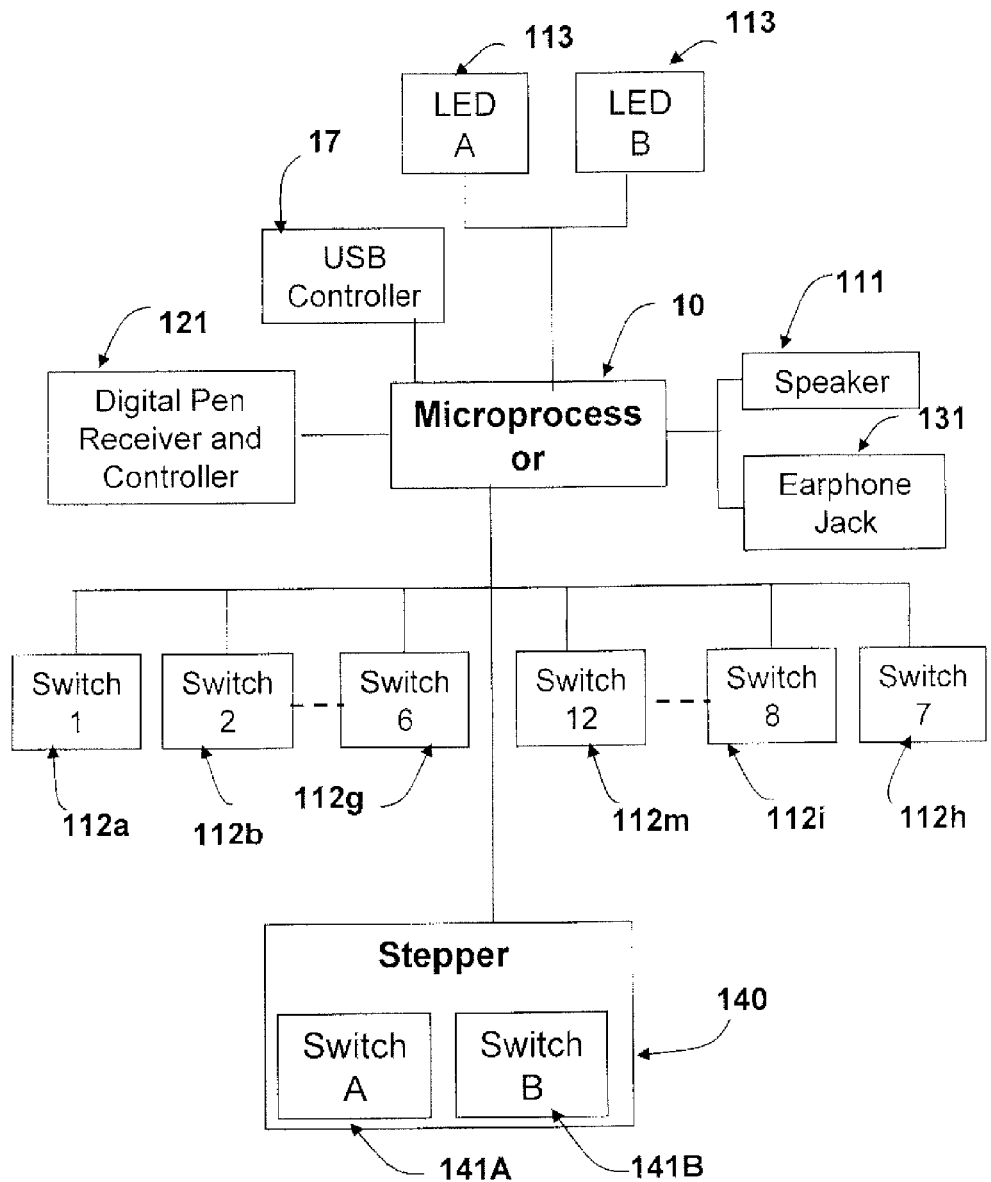

FIG. 3 schematically illustrates an acquisition box's connections, according to some embodiments of the present invention.

Figure 4:
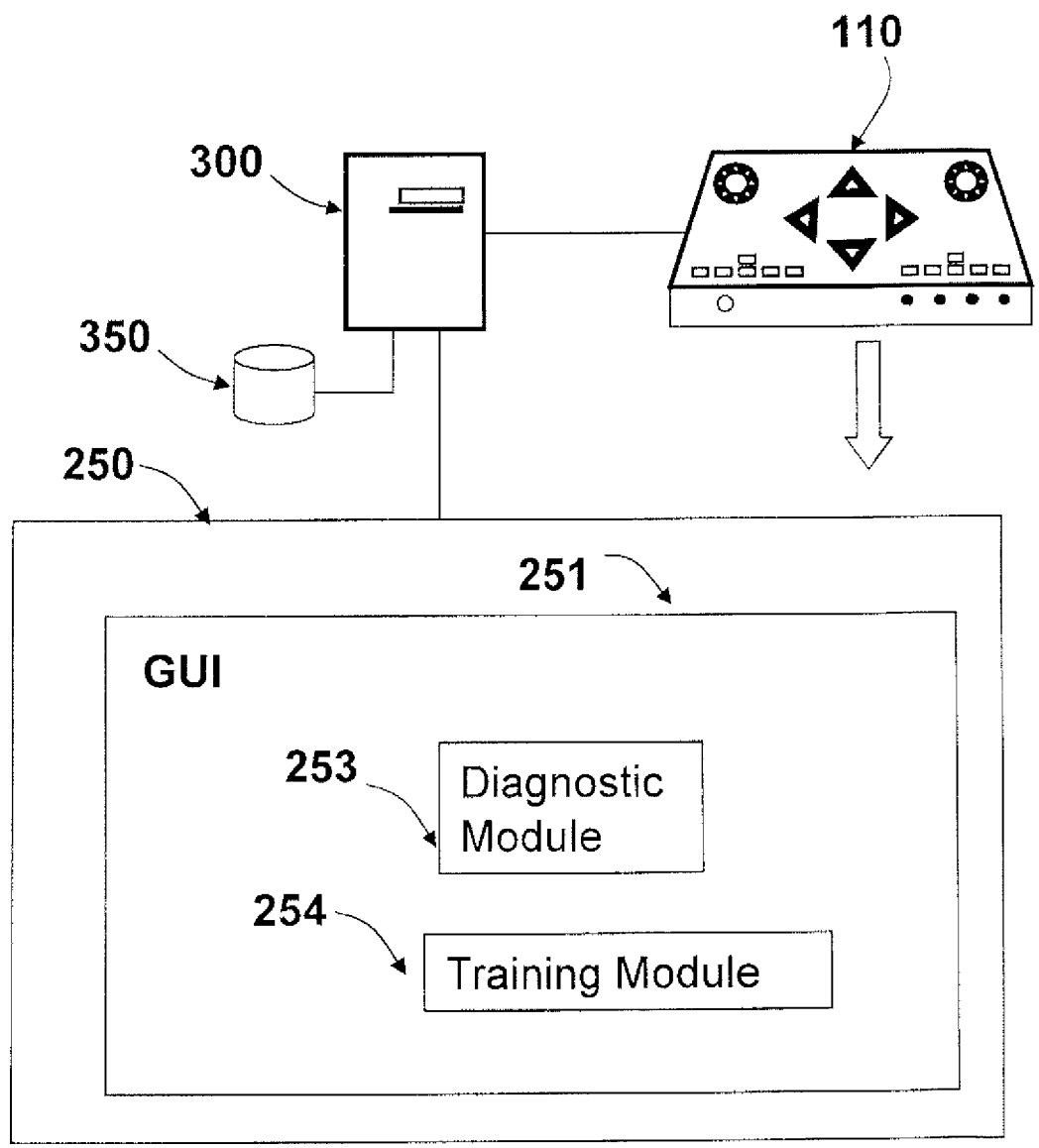

FIG. 4 schematically illustrates a software application connected to the acquisition box and to a web server, according to some embodiments of the present invention.

Figure 5:
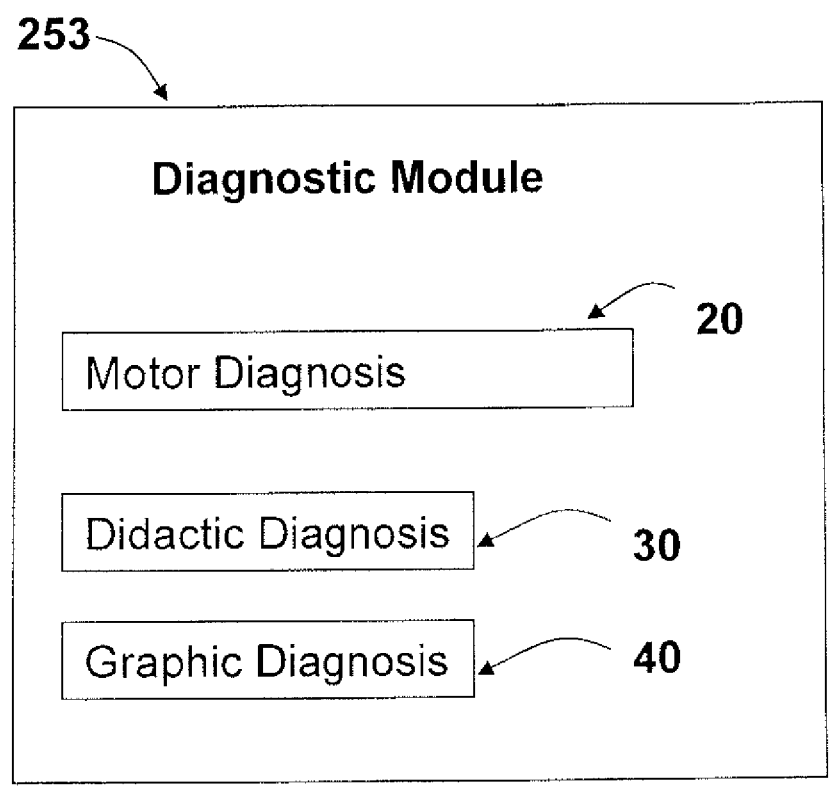

FIG. 5 schematically illustrates a diagnostic module, according to some embodiments of the present invention.

Figure 6:
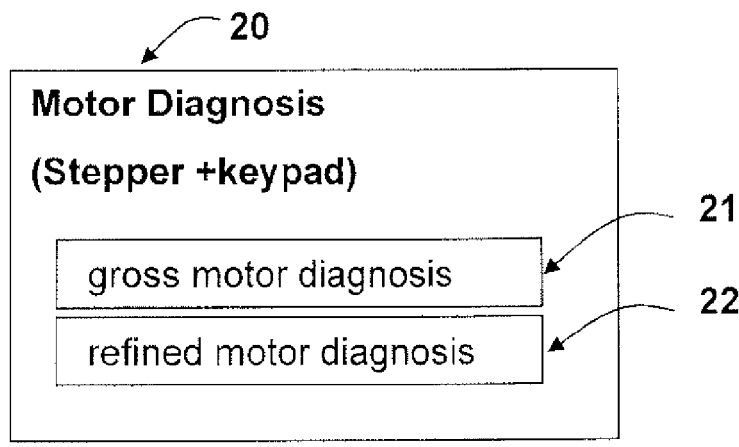

FIG. 6 schematically illustrates a motor diagnosis, according to some embodiments of the present invention.

Figure 7:
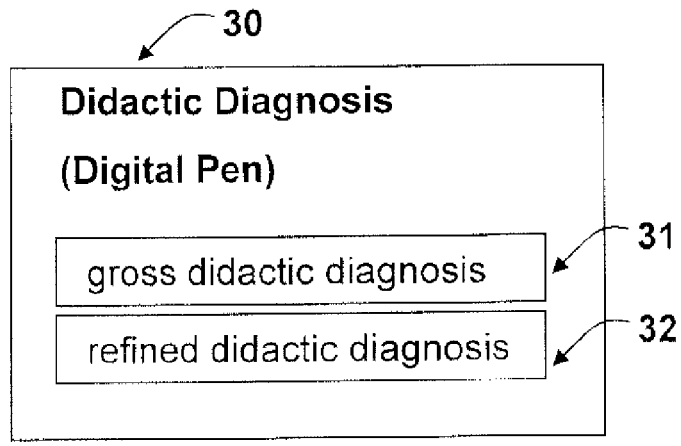

FIG. 7 schematically illustrates a didactic diagnosis, according to some embodiments of the present invention.

Figure 8:
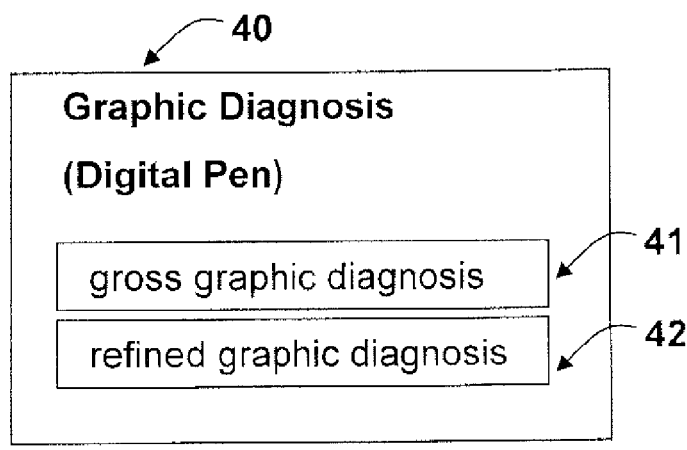

FIG. 8 schematically illustrates a graphic diagnosis, according to some embodiments of the present invention.

Figure 9:
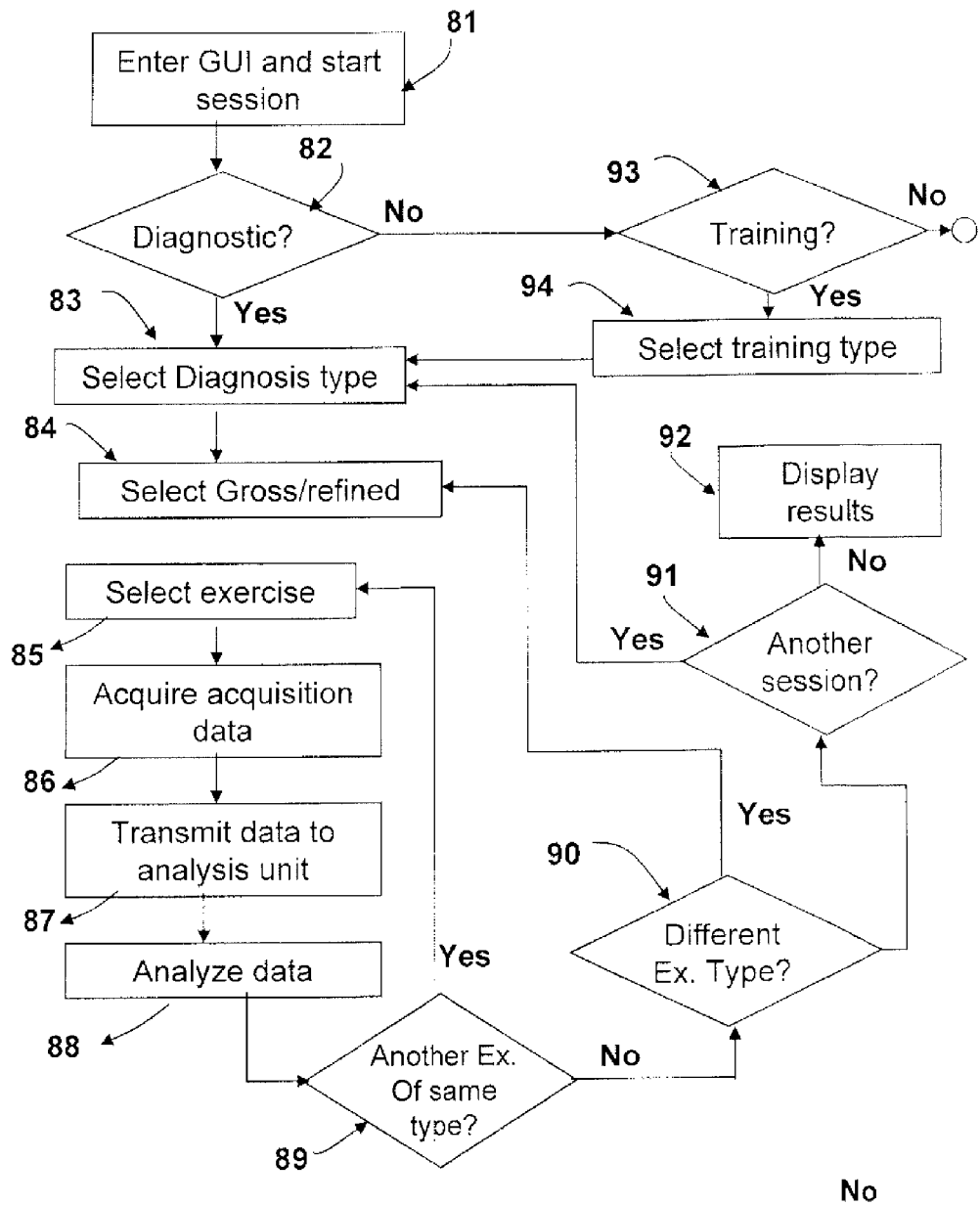

FIG. 9 is a flowchart that schematically illustrates the process of using the analysis and the acquisition units through a graphical user interface's options, according to some embodiments of the present invention.

Figure 10:
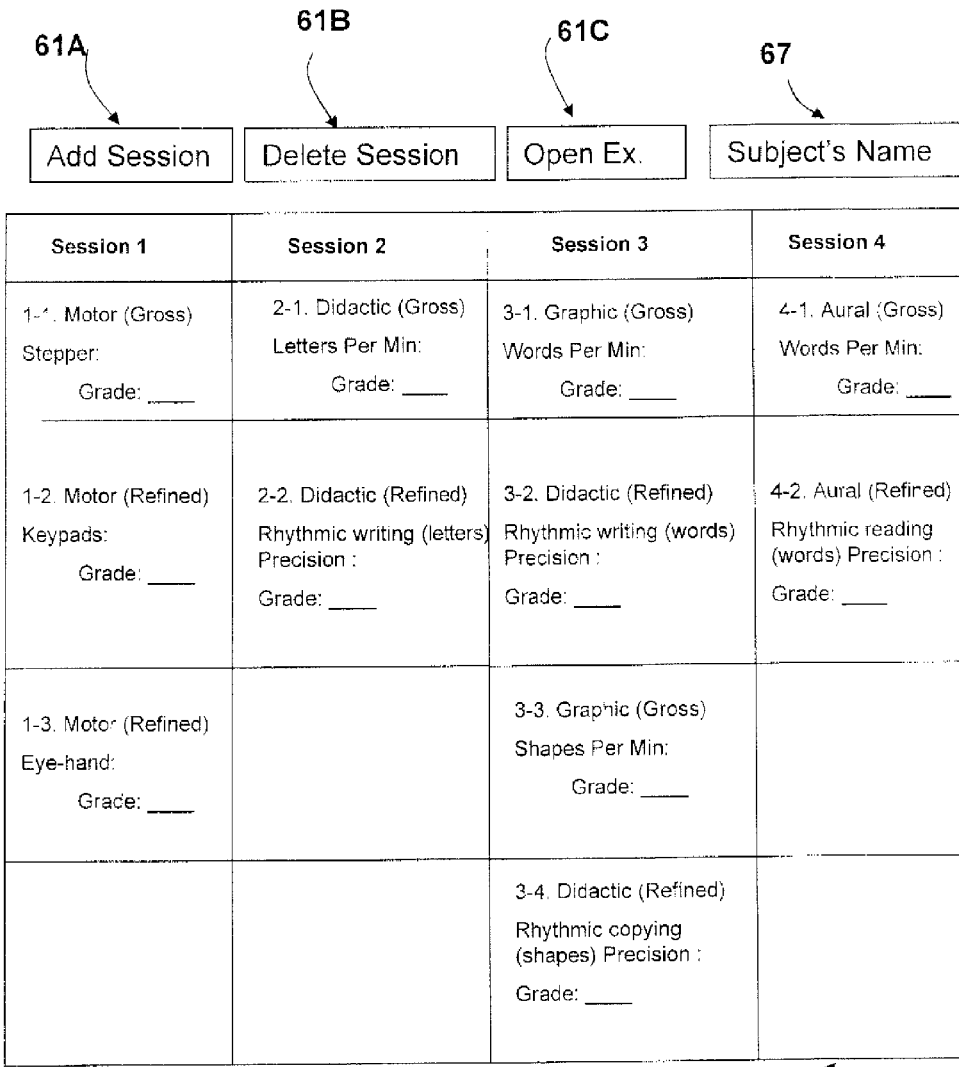

FIG. 10 schematically illustrates a display chart of sessions, exercises and exercises' results, according to some embodiments of the present invention.

Figure 11:
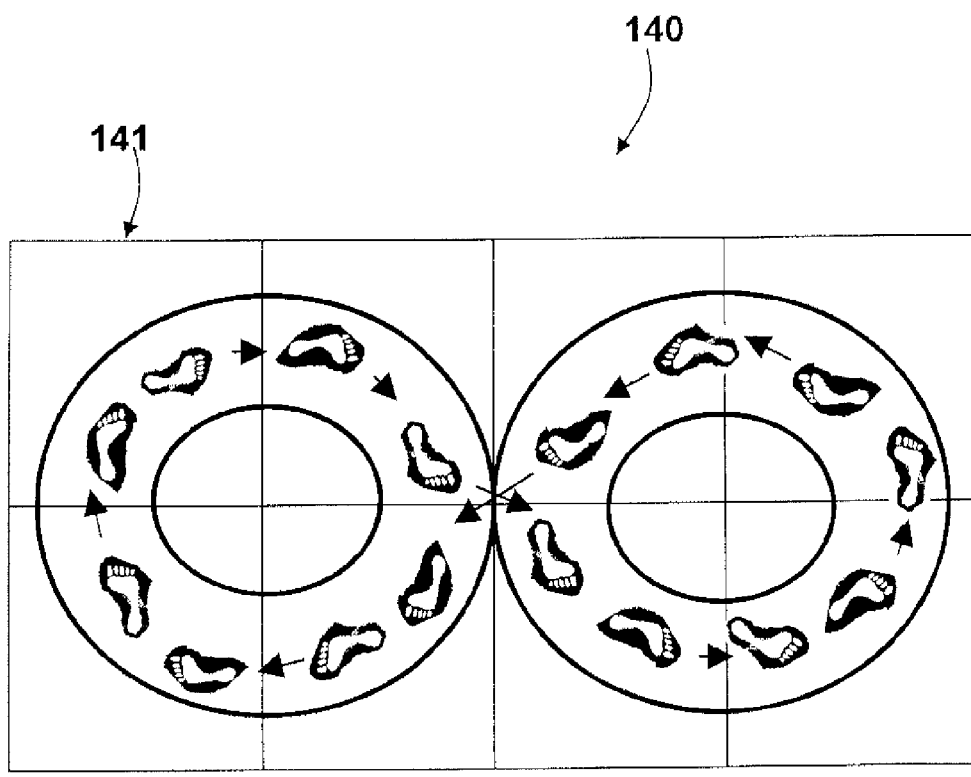

FIG. 11 schematically illustrates a stepper, designed as an eight-shaped walking platform, according to some embodiments of the present invention.

The drawings together with the description make apparent to those skilled in the art how the invention may be embodied in practice.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

DETAILED DESCRIPTIONS OF SOME EMBODIMENTS OF THE INVENTION

The present invention is a system and a method for measuring, analyzing and presenting of neuromotor functioning-assessments of at least one subject to facilitate in assessing the subject's learning and behavioral skills by measuring the subject's neuromotor performances, using various measuring devices used according to various exercising techniques. The system may comprise an acquisition unit 100 and an analysis unit 200, where the two units may be connected by any communication means known in the art to allow transmission of data.

According to some embodiments of the present invention, the acquisition unit 100 may include measuring devices that may allow measuring the subject's performances of predefined exercises that include rhythmic operation of actions that involve using those devices.

Additionally, at least part of the actions of each exercise may be performed according to a predefined rhythmus applied to the subjects through aural and/or visual indications. For example, the system may produce a metronomic tapping sound transmitted to the subject by aural means such as speakers 111 and/or earphones 130, where the system may require the subject to perform the actions according to the rhythm that is produced.

The acquisition unit 100 may measure the timing parameters (in predefined precisions), in which the subject has performed the actions required by the exercise as well as the shifts between the original rhythmus produced by the system and the subject's timing parameters acquired by the acquisition unit 100.

A user may operate the system and control the rhythm of the rhythmus producer by using tuning means 118 installed in the system. The user may be any person that tests the subject's neuromotor performances. For example, the user may be a teacher, a psychologist, a parent, etc. The subject may be any person that is tested by the system such as, for example, a child, a toddler, an adolescent child, an adult, a person with learning or motor disabilities and the like.

While the description below contains many specifications, these should not be construed as limitations on the scope of the invention, but rather as exemplifications of the preferred embodiments. Those skilled in the art will envision other possible variations that are within its scope. Accordingly, the scope of the invention should be determined not by the embodiment illustrated, but by the appended claims and their legal equivalents.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

The principles and uses of the teachings of the present invention may be better understood with reference to the accompanying description, figures and examples. It is to be understood that the details set forth herein do not construe a limitation to an application of the invention. Furthermore, it is to be understood that the invention can be carried out or practiced in various ways and that the invention can be implemented in embodiments other than the ones outlined in the description below.

It is to be understood that the terms "including", "comprising", "consisting" and grammatical variants thereof do not preclude the addition of one or more components, features, steps, or integers or groups thereof and that the terms are to be construed as specifying components, features, steps or integers. The phrase "consisting essentially of", and grammatical variants thereof, when used herein is not to be construed as excluding additional components, steps, features, integers or groups thereof but rather that the additional features, integers, steps, components or groups thereof do not materially alter the basic and novel characteristics of the claimed composition, device or method.

If the specification or claims refer to "an additional" element, that does not preclude there being more than one of the additional element. It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques and procedures either known to or readily developed from known manners, means, techniques and procedures by practitioners of the art to which the invention belongs. The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined. The present invention can be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

FIG. 1 schematically illustrates a system for neuromotor functioning assessment and training facilitating in diagnosing of the subject's behavioral functioning and learning skills, according to some embodiments of the present invention. According to these embodiments, the system may comprise:
  an acquisition unit 100 that may enable producing rhythmic aural and visual stimulation and measuring the subject's performances and responses under these stimulations, where the performances and responses may be carried out according to predefined exercises using predefined measuring devices;
  at least one analysis unit 200 that may include a software application 250 that allows receiving, storing and analyzing of acquisition data arriving from the acquisition unit 100.

According to some embodiments of the present invention, as illustrated in FIG. 1, the acquisition unit 100 may comprise, a graphic-tool 120 such as a digital pen 121 connected to at least one pen receiver 122, at least one stepper 140, at least one set of earphones 130 and at least one acquisition box 110. The graphic tool 120 may allow sensing the subject's hand movements while performing graphical exercises such as writing, drawing, etc. using the pen 120, and transmitting the sensed data to the acquisition box 110. The stepper 140 may sense the subject's steps separating one foot from the other and enabling sensing and identifying each foot's stepping impact upon each stepper's 140 pad (141A and 141B) and optionally measuring the impact's intensity as well. The stepper 140 may further transmit the measuring data to the acquisition box 110. The earphones 130 may allow the subject to hear rhythmic sounds transmitted by the acquisition box 110 while performing the actions of the exercises.

According to some embodiments of the present invention, the analysis unit 200 may comprise a processing unit 210 and a display unit 220 that allow receiving of the acquisition data from the acquisition unit 100, processing the acquisition data by comparing the acquisition data with reference associated data stored in the processing unit 210 and displaying the acquisition data, the reference data and the final analysis results.

The reference data may compose of normative values, parameters, etc. of the exercises' results adapted to a predefined grading mechanism.

According to some embodiments of the present invention, the processing unit 210 may be a computer, for example, and the display unit 220 a computer screen with a software application 250 installed.

Additionally, the system may further enable displaying of instructional information to the user to assist the user in operating the software application 250, in instructing the subject regarding the exercises in exhibiting the exercises instructions, in explaining the analysis results and their meaning etc.

According to embodiments of the present invention, as illustrated in FIG. 2, the acquisition box 110 may comprise:
  at least one speaker 111;
  visual indicators 113;
  at least one keypad 112;
  input 114 and output 115 portals;
  at least one sound tuner 118;
  a volume button 119; and
  at least one microprocessor 10.

The microprocessor 10 may comprise a sound-producer 11 and a timing unit 12. The sound producer may produce rhythmus sounds controlled by the user using the sound tuner 118 and the volume button 119 and/or the application's 250 interface through virtual control buttons and tuners. The timing unit may enable measuring and storing time related data associated with the measuring data received from the measuring devices (e.g. the stepper 140, the pen receiver 121 and the keypad 112). For example, a subject may be requested by a user to step upon the stepper 140 according to a predefined rhythmus played by the acquisition box 110 that the user can hear by using the earphones 130 and/or the speakers 111; the user may step on the stepper 140 where the timing unit 12 acquires the timing parameters of each step (meaning the time spot over the timescale) and allows measuring of the shifts between the subject's timing and the "actual" timing produced by the sound producer 11.

Depending upon embodiments of the inventions the measuring of time shifts may be carried out in the processor 10 and/or in the analysis unit 200, where the analysis unit 200 may receive the measured timing, parameters and the timing parameters of the produced rhythmus and calculate the shifts between them.

FIG. 3 schematically illustrates the acquisition boxes 110 connections, according to some embodiments of the present invention. The microprocessor 10 may be connected to the analysis unit 200 through a Universal Serial Bus (USB) controller 17. The distinguished parts of the measuring devices (e.g. the pads of the stepper 140, each keypad's 112 key and the like) may be regarded as switches. Connected to the microprocessor 10 by any communication and transmission means known in the art.

According to some embodiments of the present invention, the visual indicators 113 may be light bulbs such as light emitting diodes (LED), for example. Some of the exercises may include following the rhythmus of the top LED 113a, bottom LED 113b, left LED 113d and right LED 113d as illustrated in FIG. 2. The subject may be requested, for example, to press certain keys on the left and/or right keypads 112 using certain specified fingers, according to a predefined rhythmus indicated by the flickering of the LED indicators 113 and/or a rhythmic sound.

FIG. 4 schematically illustrates the software application 250 connected to the acquisition box 110, according to some embodiments of the present invention. The application 250 may include a graphical user interlace (GUT) 251 to allow graphically displaying of information, data and analysis results. The GUI 251 may comprise a diagnostic module 253 to enable displaying and distinguishing the exercises and the exercises' diagnostic purposes and a training module 254 that to enable setting up a training program according to the subject's diagnostic performances and the subject's personal details (e.g. the subjects' age physical condition and the like).

FIG. 5 schematically illustrates a diagnostic nodule 253, according to some embodiments of the present invention. The diagnostic module may comprise:
  a motor diagnosis 20 enabling to display exercises and exercises' results relating to the subject's neuromotor functioning using the stepper 140 and the keypad 112 as the substantially main measuring devices;
  a didactic diagnosis 30 that involves exercises that may assess and train the subject's didactic skills such as writing using the digital pen 120 and pen receiver 121 as the main measuring devices; and
  a graphic diagnosis 40 that involves exercises that may assess and train the subject's graphic skills and their consequent neuromotor skills such as drawing, copying of shapes and the like using the digital pen 120 and the pen receiver 121 as the main measuring devices.

FIG. 6 schematically illustrates the motor diagnosis 20, according to some embodiments of the present invention. The motor diagnosis 20 may comprise of two main exercises types:
  (1) A gross motor diagnosis 21 that may involve exercises in which the subject may be required to step on the stepper 140 while hearing various rhythmus beats (using the earphones 130 and/or the speakers 111) with the purpose to try and follow the rhythmus with his/her stepping over the steppers 140 pad. The acquisition box 110 may measure the timing parameters of the subject's steps and record the real timing parameters of the produced rhythmus where the processing unit 210 may analyze the acquisition data and calculate the time-shifts between the real and the acquired parameters; and
  (2) A refined motor diagnosis 22 that may involve exercises in which the subject may be required to follow both an aural and a visual rhythmic indications (that may follow the same rhythmus) in order to press keys on the keyboards 112. Theses exercises may require pressing specific fingers over specific keys according to the position of the visual indication manifested through the visual indicators 113.

FIG. 7 schematically illustrates the didactic diagnosis 30, according to some embodiments of the present invention. The didactic diagnosis 30 may comprise of two main exercises types:
  (1) Gross didactic diagnosis 31 in which the subject may be required to write down the ABC letters according to their natural sequence, where the system may measure the amount of correct and incorrect letters written and the time interval that took the subject to write them. This may be calculated into an average number of letters per minute that may be used for a gross didactic diagnosis of the subject's learning skills, for example.
  (2) Refined didactic diagnosis 32 in which the subject may be required to write down the ABC letter according to their natural sequence, using the graphic tool 120, and according to a played rhythmus where the system may measure the number of "lifts" the user has made where "lifts" are defined hereinafter when the subject lifts the graphic tool 120 when writing. For example, when writing the letter A the subject may lift the tool 120 once between the triangle and the middle line and the second time to move on to the next letter. In the refined diagnosis 32, the system may further measure and calculate the timing shifts between the original played rhythmus and the subject's lifts timing.

FIG. 8 schematically illustrates the graphic diagnosis 40, according to some embodiments of the present invention. The didactic graphic 40 may comprise of two main exercises types:
  (1) a gross graphic diagnosis 41 in which the subject may be required to copy written text and/or to copy predefined number of predefined shapes, where the system may measure the number of correct and incorrect words and/or shapes the subject has managed to accomplish per a predefined timeframe (e.g. the number of correct words per minute).
  (2) a refined graphic diagnosis 41 in which the subject may be required to copy written text and/or to copy predefined number of predefined shapes, using the graphic tool 120, according to a predefined rhythmus, where the system may measure the same parameters as in the gross diagnosis 41 as well as the timing shifts between the original played rhythmus and the subject's lifts timing.

Additionally, the diagnostic module 253 may further comprise an attentiveness-area (AA) diagnosis, according to some embodiments of the present invention. The AA diagnosis may allow testing the optimal sitting position of the subject in a classroom, for example, by testing the subject's natural listening/hearing optimum, sight optimum etc. For example by testing which ear is instinctively turned towards a sound source, which eye instinctively turns towards a light source etc. The user who examines the subject may input the results of all these "focus tests" into the application 250 using the GUI 251 selections where the application 250 may output the resulting position out of predefined classroom where the user selects the number of seats, rows and columns.

Additionally, the diagnostic module 253 may further comprise a "naming" diagnosis, according to some embodiments of the present invention. In the naming diagnosis, the subject may be required to read out from a predefined text where the system may measure the number of correct and the number of incorrect words read by the user, the time interval the reading required to enable calculating the number of correct words read per a predefined time interval etc.

According to embodiments of the present invention, to allow a more refined naming, diagnosis, the acquisition unit 100 may additionally comprise recording devices and word analyzing hardware and/or software tools to enable measuring timing shift of words from a predefined rhythmus aurally and/or visually indicated to the subject by the acquisition box 110.

According to some embodiments of the present invention, the acquisition unit 100 may be connected to the user's computerized system 200 where the computerized system ma/y be connected to a web server 300 that may maintain a website through which a web application 250 containing a web GUI 251 may allow the user to enter a personal account in which he/she may store subjects' acquisition data. Additionally, the server 300 may provide the user with an access to at least one database 350 enabling a multiplicity of users to share the same reference data, exercises instructions, reference results and the like.

FIG. 9 is a flowchart that schematically illustrates the process of using the analysis 200 and the acquisition 100 units through the GUI 251 options, according to some embodiments of the present invention. The process may comprise the steps of:

entering the GUI 251 and starting a new session 81—where to enter the application's 250 GUI 251 the user may be required to enter a website and/or to open a client program installed in his/her personal computer (depending on embodiments of the invention);

the GUI 251 may require the user to select a diagnostic 82 or a training 91 process;

upon selecting of the diagnostic process, the user may be required to select the diagnosis type 83, for example, according to the diagnosis types distinctions mention above (e.g. didactic, graphic etc.);

upon selecting the diagnostic type, the user may be required to select the exercises' type 84 (e.g. gross or refined) where a list of exercises may automatically be displayed allowing the user to— select an exercise 85;

acquiring the acquisition data 86, where the user may instruct the subject regarding the exercise and the usage of the exercise related measuring devices and indications, operate the relevant features of the acquisition box 110 and/or the relevant devices and allow the subject to perform the actions of the exercise. While the subject performs the exercise, the acquisition box 110 may online record all timing parameters and other device and exercise related data (e.g. pen 121 lifts/stepper's 140 impacts, original indication rhythmus etc.).

Transmitting the acquisition data to the analysis unit 87 for further processing;

analyzing the acquisition data 88 by, for example, comparing the acquisition data or a processed acquisition data to a reference data stored and/or retrieved by the analysis unit 200;

once the analysis of the exercise is completed, the user may select another exercise of the same type 89, another exercise of the same diagnostic type but of a different exercise type 90;

once the subject has performed all the exercises set tip by the user (e.g. a tutoring psychologist) the user may select a new session 91 repeating steps 83-90.

One the user has selected all desired sessions and the subject has performed at least some of the exercises of the selected sessions the GUT 251 may display the results of the sessions and exercises in a results screen 92 as illustrated in FIG. 10.

Additionally, once the user has selected the training rout 93—the user may select the training type 94 and be presented of substantially the same types of exercises as of the diagnostic module 253 of the GUT 251.

FIG. 10 schematically illustrates a display chart of sessions, exercises and exercises' results, according to some embodiments of the present invention. The GUT 251 may allow the user to execute operations 61 such as adding a new session to the table 61A, deleting an existing session 61B, opening a new exercise 61C and the like, where the sessions and exercises are selected out of predefined lists.

Additionally, the GUI 251 may facilitate the user in saving and displaying the sessions' tables of each of the user's subjects separately specifying the subject's details 67 by displaying them whenever the subject's account is opened.

Additionally, the sessions' table may exhibit a grade of each exercise calculated according to predefined criterions based on comparison with statistics-based models, for example.

Additionally, the application 250 may enable outputting a quantified total grade or several grades relating to several fields tested, where each grade may be compared to a grades table enabling to estimate the subject's functioning level in each field. For example, a grade from one to ten indicating the dyslexia level where below five is considered dyslexia.

According to embodiments of the invention, the system may accumulate statistical data relating to the exercises results of a multiplicity of subjects tested by a multiplicity of users. The system may process this data to update and improve the reference data to which the acquisition data is compared.

FIG. 11 schematically illustrates a stepper 140, designed as an eight-shaped walking platform, according to some embodiments of the present invention. The stepper 140 may comprise a multiplicity of sensors enabling to sense the subject's footsteps and footsteps' impact intensity upon each pad 141 of the stepper 140. This stepper 140 type may be used, for example, for testing the subject's ability to walk according to an eight-shaped line where the crossing shape of the sign 8 may require operating different hemispheres and may test different neuromotor functioning levels. Additionally, the stepper's 140 exercises may require the subject to walk and/or jump along the eight-shaped markings according to a rhythmus produced by the acquisition unit 100 while performing other actions according or not according to the same rhythmus.

According to some embodiments of the invention, the stepper 140 may enable sensing of the subject's stepping and position of steps without the use of pads 141. The stepper 140 may be a seismic or an optic detector enabling to scan a predefined area and sense the subject's feet and/or legs movements.

Additionally, the graphic tool 120 may be a digitizer screen that allows detection of the subject's graphic operations by, for example, sensing a pen's pressure upon said screen.

Alternatively, the graphic tool 120 may be an optical sensor enabling to sense the subject's hand movements.

According to some embodiments of the invention, the user may control the measuring devices through the analysis unit 200 where the GUI 251 may include control options to allow the user to control various measuring devices and features. For example, the user may be enabled by the GUI 251 to control the rhythmus and volume of the sound and visual indications, turn at least some of the devices on and off through the GUI 251 etc.

Additionally, the GUI 251 may include at least one questionnaire format to allow the user to input the subject's details such as, for example, the subject's medical and psychological history, personal details such as name, sex and age, socioeconomic background, grades at school and the like. Upon filling the questionnaire, the GUI 251 may automatically open a "personal file" of the subject enabling to store all the questionnaire as well as the exercises results in this file.

Additionally, the GUT 251 may further allow the user to enter either the each subject's specific file and/or the user's workspace by requiring the user to input security codes such as a password and/or a user name.

According to some embodiments of the invention, the sound and rhythmus may be any type of musical and/or sound pieces played according to a certain rhythmus. For example, the sound may be a sound of a falling coin replayed according to a predefined rhythmus or a musical piece where the subject is requested to perform the exercise according to his/her interpretation as to what the rhythmus of the musical piece is and/or according to the piece's changing rhythms.

While the invention has been described with respect to a limited number of embodiments, these should not be construed as limitations on the scope of the invention, but rather as exemplifications of some of the preferred embodiments. Those skilled in the art will envision other possible variations, modifications, and applications that are also within the scope of the invention. Accordingly, the scope of the invention should not be limited by what has thus far been described, but by the appended claims and their legal equivalents.

What is claimed is:

1. An interactive system for neuromotor functioning assessment and training of a subject, using rhythmic-based techniques, said system comprising:
    at least one rhythmus indicator device, operable to produce rhythmic indication of a rhythmus;
    at least one measuring device operable to measure subject's performing of actions using said measuring device; wherein the at least one measuring device is a graphic tool that enables sensing the subject's hand movements when the subject uses the graphic tool for performing graphic actions selected from a group consisting of:
writing, drawing, copying of predefined shapes, and copying written text;
    a processor configured as a timing unit operable to measure shifts between the rhythmus produced by a rhythmus producer and timing in which the subject has performed the actions that comprise the graphic actions;
    an analysis unit comprising at least one computing device, operable to analyze acquisition data at least by comparing acquisition data pertaining to the measured shifts with stored reference associated data, wherein results of the analysis are results relating to the subject's neuromotor functioning; and
    a display unit, operable to display results of said analysis.

2. The system of claim 1, wherein the at least one rhythmus indicator device comprises visual indicators operable to produce visual indications according to the rhythmus.

3. The system of claim 2, further comprising a keyboard comprising multiple keys, wherein the at least one measuring device is a plurality of measuring devices, at least one of the plurality of measuring devices is operable to measure using said measuring device subject's performing of pressing fingers over specific keys of the keyboard according to the visual indications manifested through the visual indicators.

4. The system of claim 3, wherein at least one of the plurality of measuring devices is operable to measure using said measuring device subject's performing of pressing specific fingers over specific keys of the keyboard according to the visual indications manifested through the visual indicators.

5. The system of claim 2, wherein the timing unit is operable to measure shifts between different rhythmuses produced by both aural and visual rhythmic indications and timing in which the subject has performed at least some of the actions.

6. The system of claim 1, comprising at least one acquisition box remotely coupled to the analysis unit, wherein said acquisition box comprises:
    the at least one rhythmus indicator device, the at least one rhythmus indicator device comprising at least one visual indicator and a speaker operable to produce aural rhythmic indications;
    at least one keypad comprising multiple keys; and
    input and output portals.

7. The system of claim 6 further comprising a user usable tuner operable to participate in controlling, by the user of the rhythmus, the aural and visual indications.

8. The system of claim 6 wherein said keypad enables measuring the subject's pressing of each key of the multiple keys and identifying each key that has been pressed as well as measuring the timing parameters in which each distinguished key is pressed by the subject.

9. The system of claim 6, wherein the at least one measuring device is a plurality of measuring devices, at least one of the plurality of measuring devices is a stepper that is coupled to the acquisition box and which is operable to measure subject's performing of stepping action.

10. The system of claim 9, wherein the analysis unit is operable to generate:
    motor diagnosis exercises results relating to the subject's neuromotor functioning in response to the analysis unit's analysis of acquisition data received from the stepper and a keypad of the system as source measuring devices;
    didactic diagnosis exercises results pertaining to exercises that enable assessing and training of the subject's didactic skills in response to the analysis unit's analysis of acquisition data received from the graphic-tool as a source measuring device; and
    graphic diagnosis exercises results pertaining to exercises that enable assessing and training of the subject's neuromotor skills consequent to the subject's graphic skills in response to the analysis unit's analysis of acquisition data received from the graphic-tool as a source measuring device.

11. The system of claim 10 wherein the analysis unit is further operable to generate diagnosis results of an attentiveness-area (AA) diagnosis, that are results of exercises that assess a suggested high attentiveness area for the subject in a classroom.

12. The system of claim 10, wherein the analysis unit is operable to calculate a grade for each type out of the motor diagnosis exercises results, the didactic diagnosis exercises results, and the graphic diagnosis exercises results; and is further operable to provide a quantified total grade relating to several fields tested.

13. The system of claim 9, wherein said stepper enables sensing a subject's stepping along a walking path.

14. The system of claim 13 wherein said stepper enables measuring the subject's performances when the subject walks according to an aurally produced rhythmus along the walking path that is a figure-eight-shaped route.

15. The system of claim 14, wherein at least one of the plurality of measuring devices is operable to measure using said measuring device subject's performing of actions, other than walking, that are performed by the subject concurrently with walking along the walking path.

16. The system of claim 9, wherein said stepper is an optic sensor operable to sense the subject's legs and feet movements by scanning an area.

17. The system of claim 9, wherein said stepper is a seismic sensor operable to sense the subject's feet movements.

18. The system of claim 1, wherein the analysis unit is operable to enable displaying of diagnostic exercises according to the subject's details and receiving of user selection of exercises.

19. The system of claim 1, wherein said graphic-tool includes at least one digital pen and at least one pen-receiver wherein said pen enables sensing the subject's hand movements while using said pen and transmitting sensing signals to the receiver and wherein said receiver enables receiving said signals and transmitting the measured signals to the acquisition unit.

20. The system of claim 1, wherein said graphic tool is an optical sensor enabling sensing the subject's hand movements, wherein the analysis unit is operable to compare measured timing parameters of the subject's hand lifts with the timing parameters of the rhythmus.

21. The system of claim 1, wherein the at least one measuring device is a plurality of measuring devices, at least one of the plurality of measuring devices is operable to measure subject's reading of words; wherein the timing unit is operable to measure shifts between the rhythmus produced by the rhythmus producer and timing of the word reading by the subject, wherein the analysis unit is operable to generate diagnosis results relating to the subject's neuromotor functioning in response to timing of word reading by the subject.

22. The system of claim 1, further operable to accumulate statistical data relating to the exercises results of a multiplicity of subjects tested by a multiplicity of users, and to process this data to update reference data to which the acquisition data is compared by the analysis unit.

23. A method for interactive neuromotor functioning assessment and training of a subject using rhythmic-based techniques, the method comprising:
producing rhythmic indication of a rhythmus;
measuring subject's performing of actions by at least one measuring device;
wherein the at least one measuring device is a graphic tool that enables sensing the subject's hand movements when the subject uses the graphic tool for performing graphic actions selected from a group consisting of: writing, drawing, copying of predefined shapes, and copying written text;
measuring shifts between the rhythmus and timing in which the subject has performed the actions that comprise the graphic actions;
analyzing, by an analysis unit comprising at least one processing unit, acquisition data at least by comparing acquisition data pertaining to the measured shifts with reference associated data stored by a machine, wherein results of the analyzing are results relating to the subject's neuromotor functioning; and
displaying results of said analysis.

24. The method of claim 23, wherein the measuring of the subject's performing of actions comprises measuring subjects performing of graphic actions of writing the alphabet letters according to the rhythmus; wherein the measuring of the shifts comprises measuring the timing shifts between the hand lifts of the subjects when performing the writing of the alphabet letters and the timing parameters of the rhythmus.

25. The method of claim 23, further comprising generating (a) motor diagnosis exercises results relating to the subject's neuromotor functioning in response to the analysis unit's analysis of acquisition data received from a stepper and a keypad of the system as source measuring devices; (b) didactic diagnosis exercises results pertaining to exercises that enable assessing and training of the subject's didactic skills in response to the analysis unit's analysis of acquisition data received from the graphic-tool as a source measuring device; and (c) graphic diagnosis exercises results pertaining to exercises that enable assessing and training of the subject's neuromotor skills consequent to the subject's graphic skills in response to the analysis unit's analysis of acquisition data received from the graphic-tool as a source measuring device.

26. The method of claim 25, wherein the analyzing further comprises calculating a grade for each type out of the motor diagnosis exercises results, the didactic diagnosis exercises results, and the graphic diagnosis exercises results; and providing a quantified total grade relating to several fields tested.

27. The method of claim 23, wherein the measuring of shifts comprises measuring of shifts between different rhythmuses produced by both aural and visual rhythmic indications and timing in which the subject has performed at least some of the actions.

28. The method of claim 23, wherein producing comprises producing the rhythmic indication by a visual indicator operable to produce visual indications according to the rhythmus.

29. The method of claim 28, wherein the measuring of the subject's performing of actions comprises measuring of subject's pressing fingers over specific keys of a keyboard according to the visual indications manifested through the visual indicator.

30. The method of claim 23, wherein the measuring of the subject's performing of actions comprises measuring by a stepper that is operable to measure subject's performing of stepping action and which enables sensing subject's stepping along a walking path.

31. The method of claim 23, wherein the measuring of the subject's performing of actions comprises devices subject's reading of words; wherein the measuring of the shifts comprises measuring shifts between the rhythmus and timing of the word reading by the subject, wherein the analyzing comprises generating diagnosis results relating to the subject's neuromotor functioning in response to timing of word reading by the subject.

* * * * *